(12) United States Patent　(10) Patent No.: US 6,447,511 B1
Slater　(45) Date of Patent: Sep. 10, 2002

(54) BIPOLAR ENDOSCOPIC SURGICAL SCISSOR BLADES AND INSTRUMENT INCORPORATING THE SAME

(75) Inventor: Charles R. Slater, Fort Lauderdale, FL (US)

(73) Assignee: Symbiosis Corporation, Miami, FL (US)

( * ) Notice: Subject to any disclaimer, the term of this patent is extended or adjusted under 35 U.S.C. 154(b) by 996 days.

(21) Appl. No.: 08/806,386

(22) Filed: Feb. 27, 1997

Related U.S. Application Data

(62) Division of application No. 08/354,992, filed on Dec. 13, 1994.

(51) Int. Cl.$^7$ ................................ A61B 18/18
(52) U.S. Cl. .............. 606/48; 606/45; 606/49
(58) Field of Search ............... 606/45, 1, 52

(56) References Cited

U.S. PATENT DOCUMENTS

| 2,002,594 A | 5/1935 | Wappler et al. |
| 2,031,682 A | 2/1936 | Wappler et al. ............. 174/89 |
| 3,651,811 A | 3/1972 | Hildebrandt et al. |

(List continued on next page.)

FOREIGN PATENT DOCUMENTS

| EP | 0 517 243 | 12/1992 |
| EP | 0 572 131 | 12/1993 |
| EP | 0 717 966 | 6/1996 |
| RU | 342619 | 7/1972 |
| RU | 575-103 | 10/1977 |

OTHER PUBLICATIONS

Corson, "Two new laparoscopic instruments: Bipolar sterilizing forceps and uterine manipulator," *Medical Instrumental*, vol. 11, No. 1, Jan.–Feb. 1977.

Delcaration of Mark A. Rydell dated Sep. 30, 1998 (7 pages), with attached Exhibits A–I.

Declaration of David J. Parins dated Sep. 30, 1998 (6 pages), with attached Exhibits 1–6.

Declaration of Joseph A. O'Brien dated Sep. 30, 1998 (6 pages), with attached Exhibits 1–2.

Individual, Inc., "Everest Medical Announces Notice of Allowance From US Patent Office" (Jul 21, 1994) discloses status of laparoscopic bipolar scissors technology.

Undated brochure of Hemostatix Surgical Instruments discloses bipolar endoscopic scissors.

*Primary Examiner*—Michael Peffley
(74) *Attorney, Agent, or Firm*—Finnegan, Henderson, Farabow, Garrett, & Dunner, L.L.P.

(57) ABSTRACT

Endoscopic bipolar scissor blades are formed in a laminate assembly of an electrically conductive electrode, an electrically insulating material, and a metal shearing surface which is electrically insulated and physically spaced from the electrode by the insulating material which is disposed therebetween. In one embodiment, the electrode is a metal blade, while the insulating material is a ceramic which is fixed to the metal blade, and the metal shearing surface which also provides the cutting edge is of a metal material which is fixed to the ceramic. In a second embodiment, the insulating material is a molded ceramic blade, with the electrode and the metal shearing surface layer metalized or otherwise fixed to the ceramic blade. In a third embodiment, the electrode is metalized on a thin layer insulating material which is fixed onto a metallic blade. In a fourth embodiment, metallic shearing and electrode layers are laminated to opposite sides of a fiberglass material. In all embodiments, the metal cutting edges and surfaces are insulated from the electrodes, and no short circuit can form between the electrodes even though the cutting edges and shearing surfaces are metal.

40 Claims, 8 Drawing Sheets

U.S. PATENT DOCUMENTS

| | | |
|---|---|---|
| 3,920,021 A | 11/1975 | Hiltebrandt ............ 128/303.17 |
| 3,970,088 A | 7/1976 | Morrison |
| 4,003,380 A | 1/1977 | Wien |
| 4,016,881 A | 4/1977 | Rioux et al. ........... 128/303.17 |
| 4,128,099 A | 12/1978 | Bauer ........................ 128/303 |
| 4,232,676 A | 11/1980 | Herczog |
| 4,347,842 A | 9/1982 | Beale ........................ 128/276 |
| 4,370,980 A | 2/1983 | Lottick |
| 4,492,231 A | 1/1985 | Auth |
| 4,644,651 A | 2/1987 | Jacobsen |
| 4,657,016 A | 4/1987 | Garito et al. |
| 4,671,274 A | 6/1987 | Sorochenko |
| 4,754,754 A | 7/1988 | Garito et al. |
| 4,802,476 A | 2/1989 | Noerenberg et al. |
| 4,819,633 A | 4/1989 | Bauer et al. |
| 4,848,337 A | 7/1989 | Shaw et al. |
| 4,850,353 A | 7/1989 | Stasz et al. |
| 4,862,890 A | 9/1989 | Stasz et al. |
| 4,938,761 A | 7/1990 | Ensslin |
| 4,953,559 A | 9/1990 | Salerno |
| 4,958,539 A | 9/1990 | Stasz et al. |
| 5,009,656 A | 4/1991 | Reimels |
| 5,013,312 A | 5/1991 | Parins et al. |
| 5,015,227 A | 5/1991 | Broadwin et al. |
| 5,026,370 A | 6/1991 | Lottick |
| 5,035,248 A | 7/1991 | Zinnecker |
| 5,082,000 A | 1/1992 | Pincha et al. |
| 5,085,649 A | 2/1992 | Rydell |
| 5,116,332 A | 5/1992 | Lottick |
| 5,133,727 A | 7/1992 | Bales et al. |
| 5,147,356 A | 9/1992 | Bhatta |
| 5,147,357 A | 9/1992 | Rose et al. |
| 5,151,102 A | 9/1992 | Kamiyama et al. |
| 5,160,343 A | 11/1992 | Brancel et al. |
| 5,171,256 A | 12/1992 | Smith et al. |
| 5,171,311 A | 12/1992 | Rydell et al. |
| 5,174,300 A | 12/1992 | Bales et al. |
| 5,176,677 A | 1/1993 | Wuchinich |
| 5,197,963 A | 3/1993 | Parins |
| 5,197,964 A | 3/1993 | Parins |
| 5,207,675 A | 5/1993 | Canady |
| 5,217,458 A | 6/1993 | Parins |
| 5,217,460 A | 6/1993 | Knoepfler |
| 5,219,354 A | 6/1993 | Choudhury et al. |
| 5,258,006 A | 11/1993 | Rydell et al. |
| 5,300,087 A | 4/1994 | Knoepfler |
| 5,318,589 A | 6/1994 | Lichtman |
| 5,324,289 A | 6/1994 | Eggers |
| 5,330,471 A | 7/1994 | Eggers |
| 5,342,381 A | 8/1994 | Tidemand |
| 5,352,222 A | 10/1994 | Rydell |
| 5,356,408 A | 10/1994 | Rydell |
| 5,391,166 A | 2/1995 | Eggers |
| 5,395,369 A | 3/1995 | McBrayer et al. |
| 5,396,900 A | 3/1995 | Slater et al. |
| 5,403,312 A | 4/1995 | Yates et al. |
| 5,443,463 A | 8/1995 | Stern et al. |
| 5,445,638 A | 8/1995 | Rydell et al. |
| 5,451,223 A | 9/1995 | Ben-Simhon |
| 5,456,684 A | 10/1995 | Schmidt et al. |
| 5,462,546 A | 10/1995 | Rydell |
| 5,472,443 A | 12/1995 | Cordis et al. |
| 5,496,312 A | 3/1996 | Klicek |
| 5,496,317 A | 3/1996 | Goble et al. |
| 5,514,134 A | 5/1996 | Rydell et al. |
| 5,527,313 A | 6/1996 | Scott et al. |
| 5,531,744 A | 7/1996 | Nardella et al. |
| 5,540,685 A | 7/1996 | Parins et al. |
| 5,562,659 A | 10/1996 | Morris |
| 5,569,243 A | 10/1996 | Kortenbach et al. |
| 5,573,534 A | 11/1996 | Stone |
| 5,573,535 A | 11/1996 | Viklund |
| 5,611,813 A | 3/1997 | Lichtman |
| RE36,795 E | 7/2000 | Rydell- |

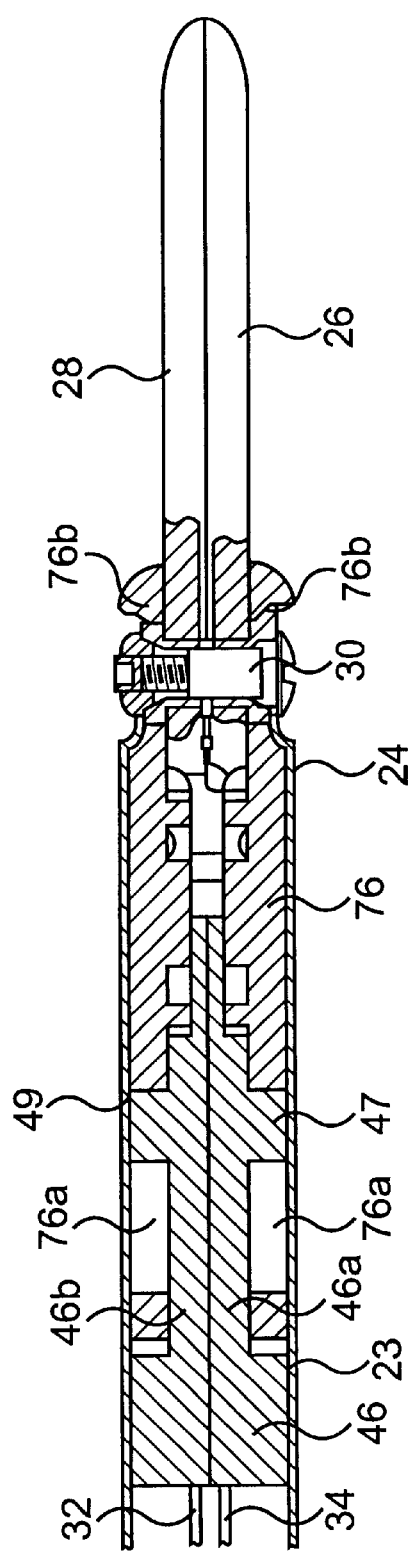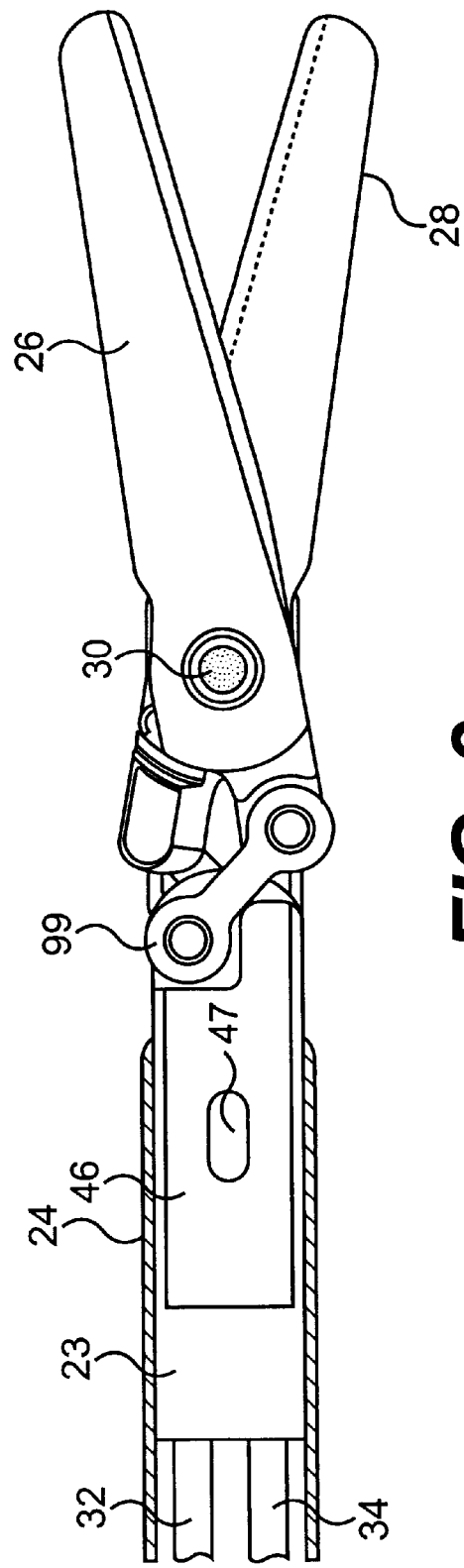
FIG. 3a
FIG. 3

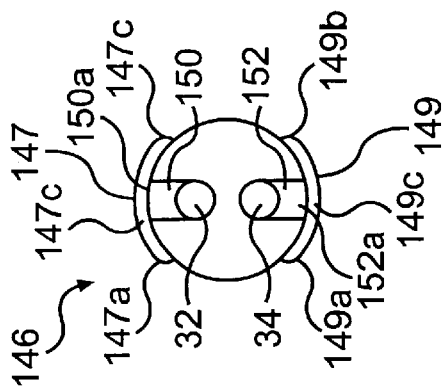
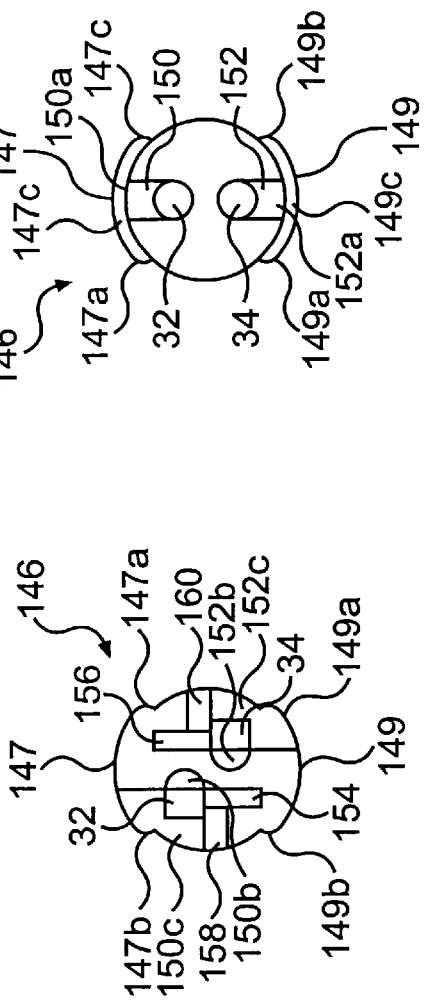
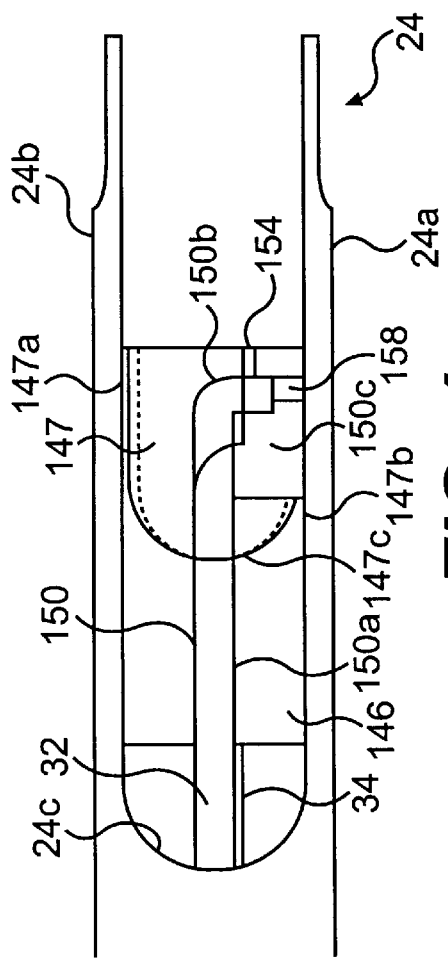
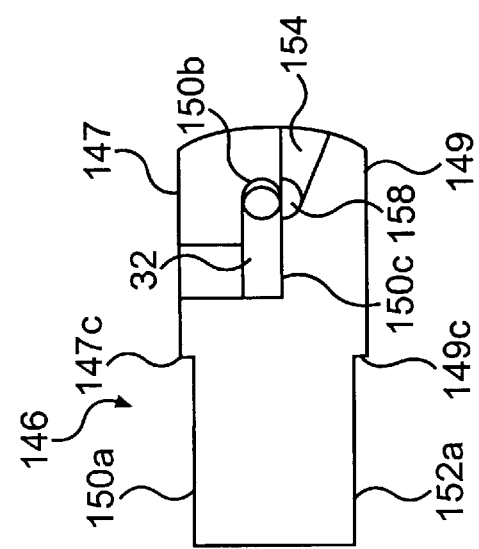

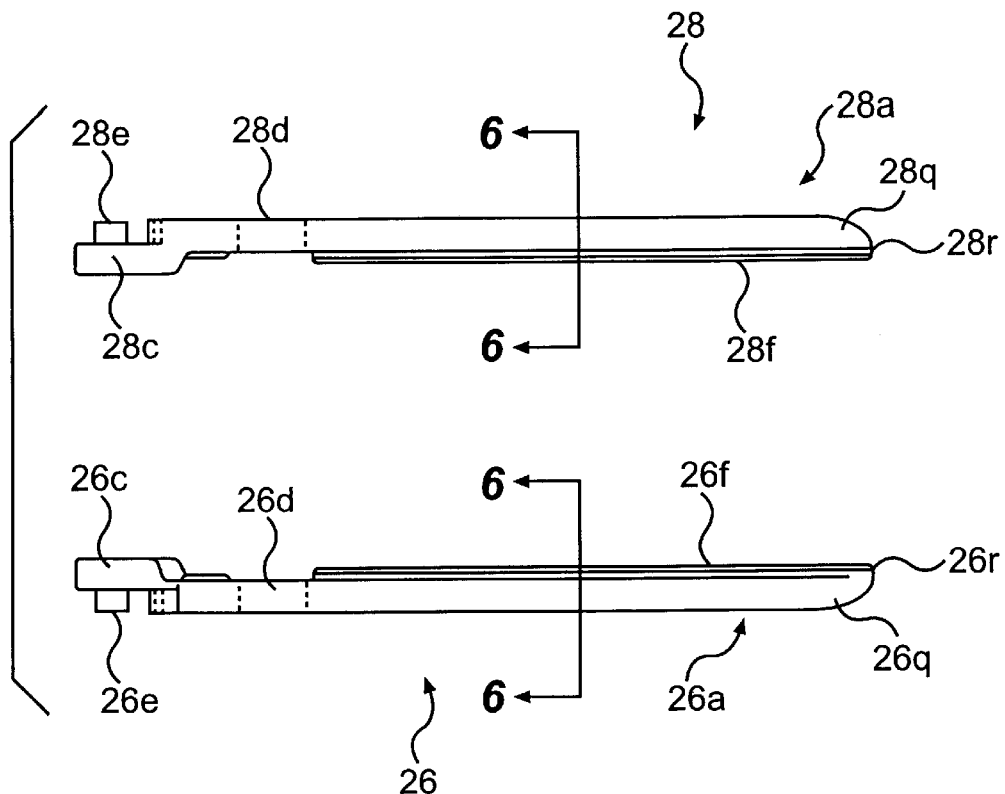
FIG. 5
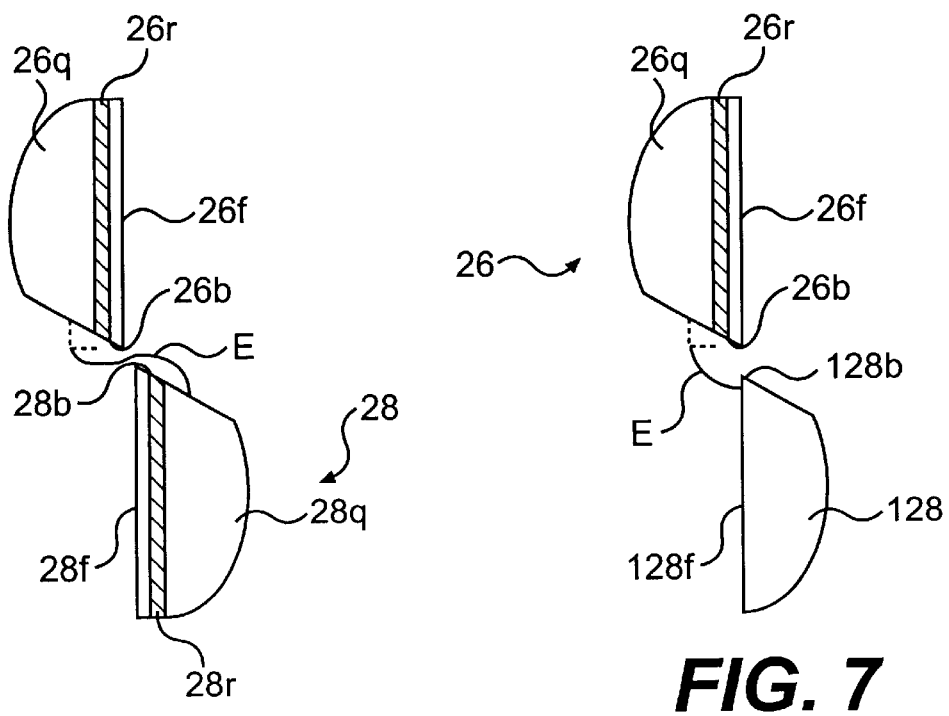
FIG. 6
FIG. 7

BIPOLAR ENDOSCOPIC SURGICAL SCISSOR BLADES AND INSTRUMENT INCORPORATING THE SAME

This is a division of application Ser. No. 08/354,992, filed Dec. 13, 1994.

BACKGROUND OF THE INVENTION

1. Field of the Invention

The present invention relates generally to endoscopic surgical instruments. More particularly, the invention relates to an endoscopic surgical instrument having end effectors made out of a combination of conductive and non-conductive materials. The invention has particular use with respect to bipolar endoscopic cautery. For purposes herein, the term "endoscopic instruments" is to be understood in its broadest sense to include laparoscopic, arthroscopic, and neurological instruments, as well as instruments which are inserted through an endoscope.

2. State of the Art

Endoscopic surgery is widely practiced throughout the world today and its acceptance is growing rapidly. In general, endoscopic/laparoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. These instruments generally comprise a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like. Because of their very small size and the requirements of strength and/or sharpness, end effectors are difficult to manufacture and are typically formed of forged stainless steel. As such, they form an expensive portion of the endoscopic instrument.

Modern endoscopic procedures often involve the use of electrocautery, as the control of bleeding by coagulation during surgery is critical both in terms of limiting loss of blood and in permitting a clear viewing of the surgical site. As used herein, cautery, electrocautery, and coagulation are used interchangeably. Several types of electrocautery devices for use in endoscopic surgery are described in the prior art. Monopolar electrosurgical instruments employ the instrument as an electrode, with a large electrode plate beneath end in contact with the patient serving as the second electrode. High frequency voltage spikes are passed through the instrument to the electrode (i.e., end effector) of the endoscopic instrument to cause an arcing between the instrument and the proximate tissue of the patient. The current thereby generated continues through the patient to the large electrode plate beneath the patient. Monopolar cautery has the disadvantage that the current flows completely through the patient. Because control of the current path through the body is not possible, damage can occur to tissue both near and at some distance from the surgical site. In addition, it is has been observed that monopolar cautery can result in excessive tissue damage due to the arcing between the end effector and the tissue.

In order to overcome the problems associated with monopolar cautery instruments, bipolar instruments have been introduced. In bipolar electrosurgical instruments, two electrodes which are closely spaced together are utilized to contact the tissue. Typically, one end effector acts as the first electrode, and the other end effector acts as the second electrode, with the end effectors being electrically isolated from each other and each having a separate current path back through to the handle of the instrument. Thus, in a bipolar instrument, the current flow is from one end effector electrode, through the tissue to be cauterized, to the other end effector electrode.

Various endoscopic instruments with cautery capability are known in the art. U.S. Pat. No. 4,418,692 to Guay, for example, discloses a device for use in laparoscopic tubal cauterization for blocking the Fallopian tubes of a patient. The device comprises a substantially tubular body member having a spring-biased piston slidably mounted therein. A pair of electrodes (either monopolar or bipolar) are disposed to grasp living tissue when the piston is in a first position biased by the spring and to release the tissue when a button is pressed which moves the piston into a second position. The device includes a circuit breaker which interrupts current flowing to the electrodes when the piston is in the second position. When the electrodes grasp the tissue, however, current is supplied to the entire surface of the electrode, that is, both the grasping surface and the outer non-grasping surface.

Another electrosurgical instrument for use in combination with an endoscope is disclosed in U.S. Pat. No. 5,007,908 to Rydell for "Electrosurgical Instrument Having Needle Cutting Electrode and Spot-Coag Electrode". Rydell's device includes an elongated flexible tubular member with a plurality of lumens. The distal end of the tubular member is provided with a bullet shaped ceramic tip covered with a conductive layer and having an opening coupled to a first one of the lumens. The conductive layer is coupled to a conductor which extends through a second one of the lumens to an electrical source. A second conductor, also coupled to the electrical source is slidable through the first lumen by a plunger. The two electrodes form a bipolar pair. In a second embodiment, the conductive layer on the ceramic tip is split by an insulating gap and both halves of the tip form a bipolar pair of electrodes. As with the Guay device, above, substantially the entire distal surface of Rydell's device serves as an electrode when energized.

Several hemostatic bipolar electrosurgical scissors have also been described. U.S. Pat. No. 3,651,811 to Hildebrandt describes a bipolar electrosurgical scissors having opposing cutting blades forming active electrodes. The described scissors enables a surgeon to sequentially coagulate the blood vessels contained in the tissue and then to mechanically sever the tissue with the scissor blades. In particular, with the described bipolar electrosurgical scissors, the surgeon must first grasp the tissue with the scissor blades, energize the electrodes to cause hemostasis, de-energize the electrodes, and then close the scissor blades to sever the tissue mechanically. The scissors are then repositioned for another cut accomplished in the same manner. With the bipolar electrosurgical scissors of Hildebrandt, the surgeon cannot maintain the electrodes in a continuously energized state because the power supply would be shorted out and/or the blades damaged if the blades are permitted to contact each other while energized.

The disadvantages of the bipolar scissors of Hildebrandt are overcome by the disclosure in U.S. Pat. Nos. 5,324,289 and 5,330,471 to Eggers. In its preferred embodiment, the bipolar electrosurgical scissors of Eggers comprise a pair of metal scissor blades which are provided with an electrically insulating material interposed between the shearing surfaces of the blades so that when the scissor blades are closed, the metal of one blade never touches the metal of the other blade, i.e., the insulating material provides the cutting edge and the shearing surface. With the arrangement provided by Eggers, a cautery current will pass from the top back edge of the bottom metal blade through the tissue which is to be cut and to the bottom back edge of the top metal blade directly in advance of the cutting action. As the scissors are gradually closed, the hemostasis preferentially occurs at a location just in advance of the cutting point which itself moves distally along the insulated cutting edges of the blades in order to sever the hemostatically heated tissue. With this arrangement, the scissors may be maintained in a continuously energized state while performing the cutting. The Eggers patent describes various alternative embodiments of the bipolar scissors, including the use of metal blades with only one blade being insulated on its shearing surface, and the use of insulating blades with back surfaces coated with metal.

SUMMARY OF THE INVENTION

It is therefore an object of the invention to provide a pair of scissor blades for a bipolar cauterizing surgical scissors which provide a metal on metal cutting/shearing action.

It is another object of the invention to provide a pair of scissors blades for a bipolar cauterizing surgical scissors which have shearing surfaces that are insulated from cautery surfaces.

It is also an object of the invention to provide an endoscopic bipolar cauterizing scissors which provides a metal on metal cutting action and which may be either curved or flat.

In accord with the objects of the invention, the scissor blades of the present invention are comprised of an electrically conductive electrode, an electrically insulating material, and a metal shearing surface which is electrically insulated and physically spaced from the electrode by the insulating material which is disposed therebetween. The scissor blades, for example, may comprise but are not limited to a composite assembly of an electrode layer, an insulating layer, and a metal shearing surface layer. In the presently preferred embodiment, the electrode layer is a metal blade which is typically constructed from stainless steel, while the insulating layer is a ceramic which is deposited, bonded, or otherwise fixed on the metal blade, and the metal shearing surface layer which also provides the cutting edge is a metal (e.g., copper, gold, stainless steel etc.) which is metalized, deposited, sputtered, plated, bonded, or otherwise fixed onto the ceramic. In a second embodiment, the insulating layer is a ceramic support, with the electrode layer and the metal shearing surface layer being metalized, deposited, sputtered, plated, bonded, or otherwise fixed to the ceramic support. In a third embodiment, the insulating layer is deposited, bonded, or otherwise fixed onto a metal blade which includes the cutting edge and shearing surface, while the electrode metal layer is metalized, deposited, sputtered, plated, bonded, or otherwise fixed onto the insulating layer. In a fourth embodiment, the insulating layer is a composite material such as fiberglass which is provided with metal electrode and metal shearing surface layers which are metalized, deposited, sputtered, plated, bonded, or otherwise fixed onto opposite sides of the fiberglass layer. In all embodiments, since the metal cutting edges and shearing surfaces are insulated from the electrodes, no short circuit can form between the electrodes even though the cutting edges and shearing surfaces are metal.

As the scissor blades are intended for use as part of an endoscopic instrument, each blade is preferably provided with a first hole which receives an axle or clevis pin around which the blades rotate. In addition, each blade is preferably provided with a pin or protrusion extending from a proximal or base portion of the blade. The pins are provided to receive links which couple the blades to an actuator mechanism.

The endoscopic bipolar cautery scissors instrument which utilizes the blades of the invention is substantially as is described in copending application U.S. Ser. No. 08/284,793, the complete disclosure of which is hereby incorporated by reference herein, and utilizes a push rod assembly with two conductive push rods which are stabilized and insulated relative to each other. The distal ends of the push rods are coupled to the end effectors by the links. The proximal ends of the push rods extend through the handle and lever of the scissors instrument and present electrical cautery pins onto which a standard bipolar cautery plug can be mated.

Additional objects and advantages of the invention will become apparent to those skilled in the art upon reference to the detailed description taken in conjunction with the provided figures.

BRIEF DESCRIPTION OF THE DRAWINGS

FIG. 3 is an enlarged broken side elevation view in partial section of the distal end of the instrument of FIG. 1;

FIG. 3a is an enlarged broken top view in partial section of the distal end of the instrument of FIG. 1;

FIG. 4 is a view similar to FIG. 3a of a second embodiment of a distal push rod collar;

FIG. 4a is a side elevation view of the collar of FIG. 4;

FIG. 4b is a distal end view of the collar of FIG. 4a;

FIG. 4c is a proximal end view of the collar of FIG. 4a;

FIG. 5 is an enlarged top view of a first embodiment of scissor blades according to the invention;

FIG. 6 is a cross sectional view of the scissor blades of FIG. 5 taken along lines 6—6 and shown in their operating positions;

FIG. 7 is a view similar to FIG. 6 but showing one of the scissor blades of FIGS. 5 and 6 in use with a conventional scissor blade in an alternative first embodiment;

DETAILED DESCRIPTION OF THE PREFERRED EMBODIMENTS

Figure 1:
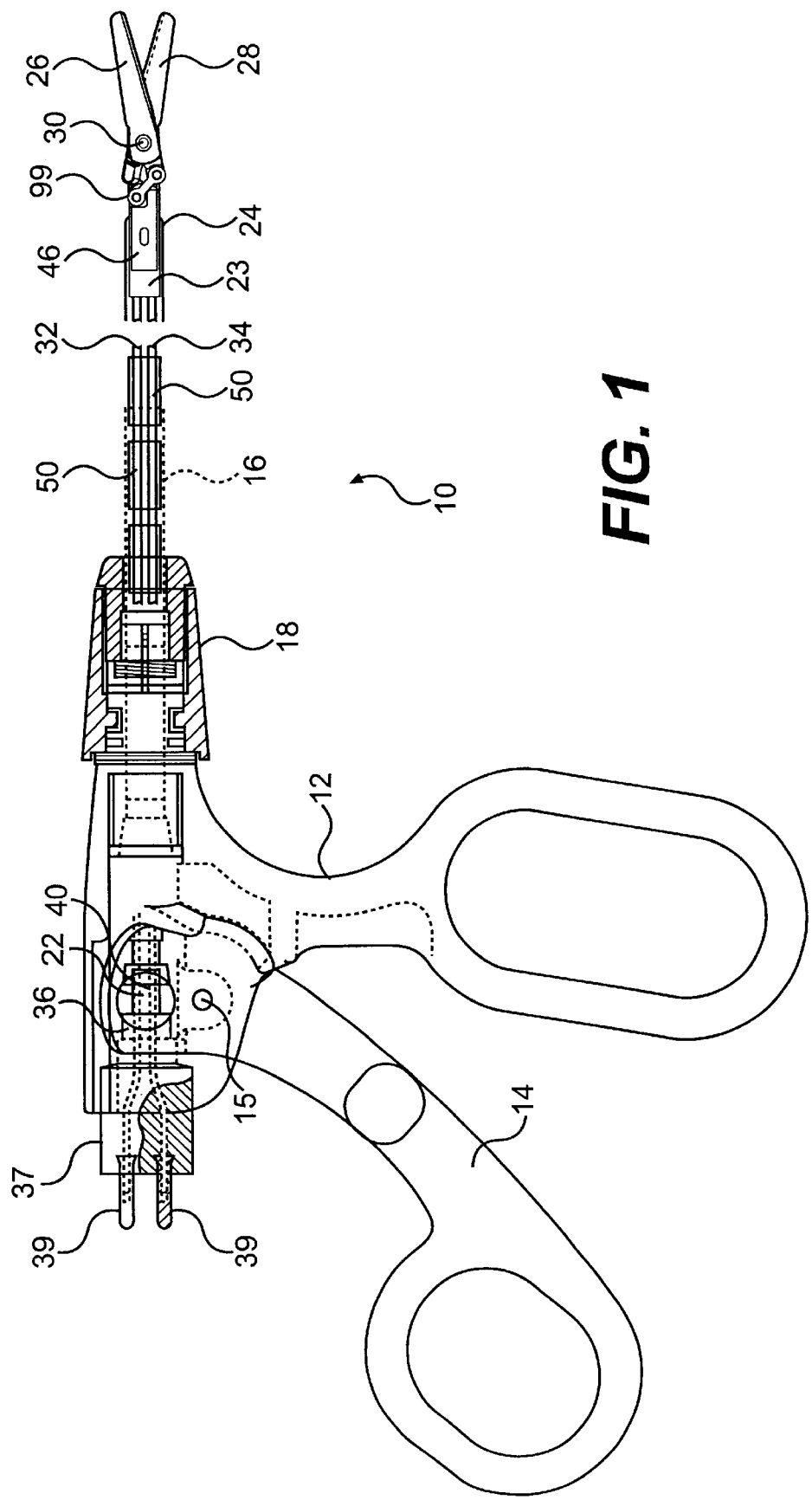
FIG. 1 is a broken side elevation view in partial section of an endoscopic bipolar scissors instrument according to the invention.
Figure 2:
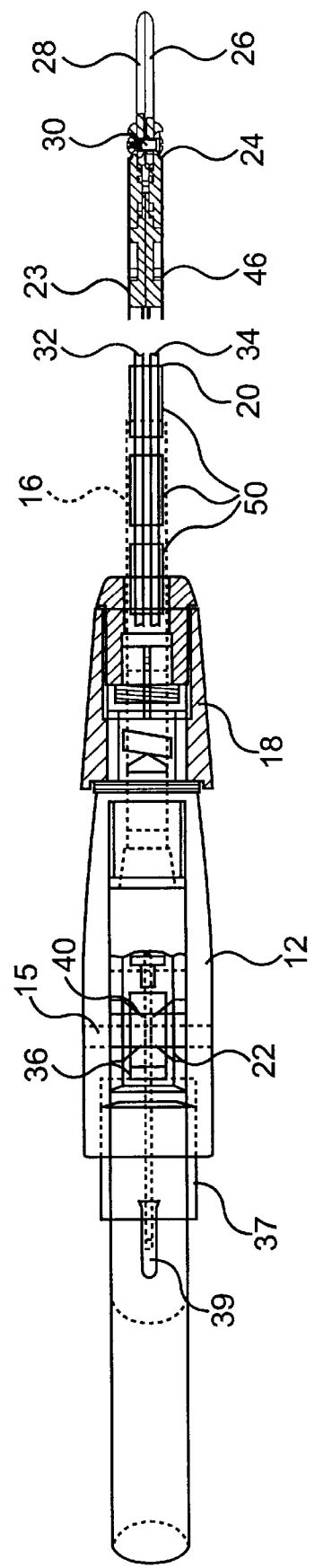
FIG. 2 is a broken top view in partial section of the instrument of FIG. 1.

Turning now to FIGS. 1 through 3a, an endoscopic bipolar scissors instrument 10 includes a proximal handle 12 with a manual level actuator 14 pivotally coupled to the handle by a pivot pin 15. A hollow stainless steel tube 16 is rotatably coupled to the handle 12 and is preferably rotatable about its longitudinal axis relative to the handle 12 through the use of a ferrule 18 such as described in detail in previously incorporated copending application Ser. No. 08/284,793. A push rod assembly 20 extends through the hollow tube 16 and is coupled at its proximal end 22 to the manual lever actuator 14 as described in more detail in copending application Ser. No. 08/284,793. The distal end of the tube 16 has an integral clevis 24 within which a pair of scissor blades 26, 28 are mounted on an axle screw 30. The distal end 23 of the push rod assembly 20 is coupled to the scissor blades 26, 28 so that reciprocal movement of the push rod assembly 20 relative to the tube 16 opens and closes the scissor blades 26, 28. It will be appreciated that the reciprocal movement of the push rod assembly 20 relative to the tube 16 is effected by movement of the manual lever actuator 14 relative to the handle 12.

The presently preferred embodiment of the push rod assembly 20 includes a pair of stainless steel rods 32, 34 which are molded into a proximal collar 36 and captured in a distal collar 46. The proximal collar has a radial groove 40 in its distal portion and an increased diameter proximal portion 37 which carries a pair of electrical coupling pins 39 which are electrically coupled to the rods 32, 34. As shown, the pins 39 are spaced farther apart from each other than the rods 32, 34 so as to accommodate a standard cautery connector. The rods 32, 34 are covered with insulating high density polyethylene (HDPE) tubes along substantially their entire length between the proximal and distal collars 36, 46. A plurality of spaced apart polypropylene cylinders 50 are molded about the rods between the proximal collar 36 and the distal collar 46. These cylinder stabilize the rods against helical twisting when the tube 16 is rotated and, by being discontinuous, prevent against warping of the push rod assembly.

According to one embodiment, and as seen best in FIGS. 3 and 3a, the distal collar 46 is made from two ceramic pieces 46a, 46b which are snap fit and bonded to each other. A pair of clevis insulators 76 are placed in the clevis as shown in FIG. 3a. Each clevis insulator 76 has a proximal side slot 76a and a distal bushing hole 76b. The collar 46 has a pair of guiding wings 47, 49 which engage slots 76a in the clevis insulators 76. The electrically conductive rods 32, 34 exit the distal collar 46 through opposite sides at substantially right angles. The distal ends of the rods 32, 34 are mechanically and electrically coupled to the respective blades 26, 28 by respective electrically conductive links 99.

According to a presently preferred embodiment, and as best seen in FIGS. 4, 4a, 4b, and 4c, a distal collar 146 is a single ceramic unit which is substantially circular in cross section except for upper and lower projections 147, 149. These projections engage the space between arms 24a, 24b of the clevis 24 and prevent the collar 146 from rotating in the clevis 24 and from passing beyond the proximal end 24c of the clevis 24. Consequently, the projections each have a pair of substantially parallel edges 147a, 147b, 149a, 149b and a rounded proximal edge 147c, 149c. The collar 146 has a pair of push rod receiving channels 150, 152 for receiving the push rods 32, 34 respectively. The channels have portions 150a, 152a which are radially open to the surface of the collar 146 from the proximal end thereof to a point approximately half way under the projections 147, 149. The channels 150, 152 terminate under the projections 147, 149 with a right angle bend 150b, 152b. A radial opening 150c, 152c extends proximally along each side of the collar from the right angle bend 150b, 152b to a point contiguous with the radially open part 150a, 152a of the channels 150, 152. The radial openings 150c, 152c are each substantially orthogonal to the radially open parts 150a, 152a. The distal end of the collar 146 has a pair of ramped slot openings 154, 156 which terminate at their proximal ends with substantially semicircular grooves 158, 160. The slot openings and grooves are provided to accommodate the ends of links 99 (see FIGS. 1 and 3) for coupling the distal ends of the push rods 32, 34 to scissor blades. The collar 146 is easily attached to the distal ends of the push rods 32, 34 by pressing the push rods into the radially open parts 150a, 152a of the channels 150, 152 so that the bent ends of the push rods enter the radial openings 150c, 152c. The push rods and/or the collar 146 are pushed towards each other so that the bent ends of the push rods abut the right angle bends 150b, 152b in the channels 150, 152, at which location the links 99 are coupled to the push rods.

Referring now to a first embodiment of the scissor blade invention seen in FIGS. 5 and 6, the first scissor blade 26 has a distal portion 26a, a lower proximal tang 26c, and a mounting hole 26d therebetween. A connecting lug 26e extends orthogonally outward from the surface of the tang 26c in a first direction. As shown in FIGS. 5 and 6, the distal portion 26a includes an lower cutting edge 26b and an inner surface 26f (also called the shearing surface). Behind the inner surface 26f of the first scissor blade is an insulating layer 26r, and a conducting electrode layer 26q. The opposed second scissor blade 28 is configured similarly to the first scissor blade and has a distal portion 28a, an upper proximal tang 28c, and a mounting hole 28d therebetween. A connecting lug 28e extends orthogonally from the surface of the tang 28c in a second direction which is opposite to the first direction mentioned above. The distal portion 28a includes an upper cutting edge 28b and an inner surface 28f. Behind the inner surface 28f of the second scissor blade 28 is an insulating layer 28r, and a conducting electrode layer 28q.

According to the first embodiment shown in FIGS. 5 and 6, both scissor blade assemblies 26 and 28 are laminated assemblies which include a metal support (also called a metal blade support) 26q, 28q, an intermediate electrically insulative layer 26r, 28r and a metal blade or face 26f, 28f defining a shearing surface. It will be appreciated that the metal faces 26f, 28f are preferably provided with sharpened opposed cutting edges 26b, 28b. The metal blades supports 26q, 28q form the electrically conductive portions (i.e., the electrodes) of the scissor blades through which cautery current is applied. In this regard, substantially the entire lengths of blade supports 26q, 28q are conductive, including the proximal lugs 26e which make electrical connection with the respective rods 32, 34 via links 99 as described above with reference to FIGS. 3–4c. As seen in FIG. 6, the preferential path of current flow "E" is through the metal support portions 26q, 28q of the scissor blades which are insulated from the cutting edges 26b, 28b and the shearing surfaces (faces) 26f, 28f of the blades. Because of this arrangement, cautery and coagulation current may be applied continuously throughout the cutting/shearing procedure since the contact of the cutting edges and shearing surfaces of the blades will not short circuit the device.

The embodiment shown in FIGS. 5 and 6 may be manufactured by first laminating machined or cast stainless steel, superalloy, bronze or other conductive metal blade supports 26q, 28q with the insulating layers 26r, 28r such as by gluing, glazing, spraying, depositing, firing, or otherwise fixing a ceramic to the inner surfaces of blade supports 26q, 28q. The metal faces 26f, 28f having the cutting edges and shearing surfaces may then be applied by gluing, sputtering, metalizing, thermal spraying, plating, or otherwise fixing the metal layers 26f, 28f onto the insulating layers 26r, 28r. The edges 26b, 28b may be sharpened after the laminating process is completed. The insulating layers may advantageously be made of an aluminum-oxide or another ceramic, and a nickel/aluminum coating may be advantageously applied to the blade supports to aid in bonding the aluminum-oxide ceramic insulating layers to the metallic blade supports.

From the foregoing, it will be appreciated that in order to achieve the object of preventing the cutting edges and shearing surface from short circuiting the device, it is only necessary that one of the scissor blades be constructed as described above. FIG. 7 shows an alternative to the first embodiment of the invention where one of the blades 26 of the first embodiment is used in conjunction with a conventional scissor blade 128 which is entirely conductive. In this embodiment and in the embodiments described below, similar reference numerals refer to similar elements of the embodiments. As illustrated in FIG. 7, the preferential path of current flow "E" is through the metal support portion 26q of blade 26 to the shearing surface 128f and/or cutting edge 128b of the scissor blade 128.

Figure 8:
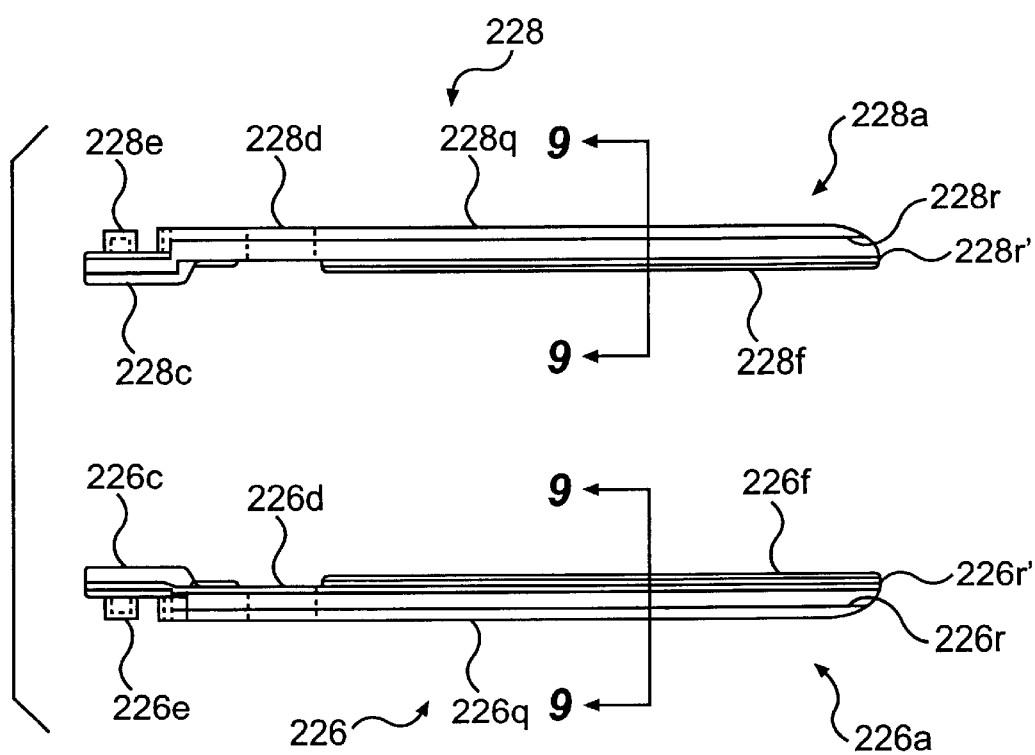
FIG. 8 is a view similar to FIG. 5 of a second embodiment of the scissor blades according to the invention.
Figure 9:
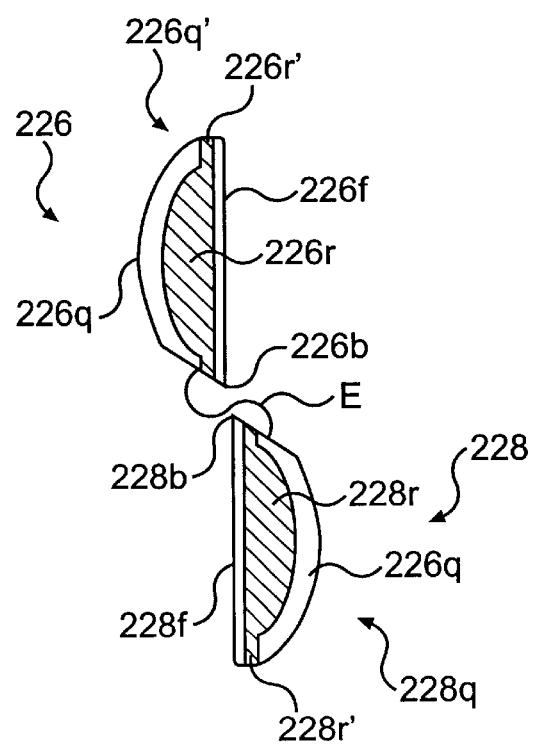
FIG. 9 is a cross sectional view of the scissor blades of FIG. 8 taken along lines 9—9 and shown in their operating positions.

FIGS. 8 and 9 show a second embodiment of scissor blades 226, 228. According to this embodiment, both scissor blades 226 and 228 are laminated assemblies which include a blade support 226q', 228q', which itself is a laminated sub-assembly of a non-conductive core support 226r, 228r and an outer metallic layer support 226q, 228q. A metal blade layer or face 226f, 228f defining a shearing surface is laminated to the inner surface of the non-conductive core 226r, 228r. It will be appreciated that the metal blade layers 226f, 228f are preferably provided with sharpened opposed cutting edges 226b, 228b. The outer metallic layers 226q, 228q of the blade supports 226q', 228q' form the electrode portions of the blades through which cautery current is applied. As seen best in FIG. 8, the outer metallic layers 226q, 228q extend along substantially the entire length of the blades (over the non-conductive cores 226r, 228r) to make an electrical connection with a source of cautery at the proximal connecting lugs 226e, 228e of the blades. As seen in FIG. 9, the path of preferential current flow "E" is through the electrode portions 226q', 228q' of the blades which are insulated from the cutting edges and the shearing surfaces of the blades. Because of this arrangement, cautery current may be applied continuously throughout the cutting procedure since the contact of the shearing surfaces of the blades will not short circuit the device.

The embodiment shown in FIGS. 8 and 9 may be manufactured by molding ceramic cores 226r, 228r and laminating both the inner and outer surfaces with metal by gluing, sputtering, metalizing, thermal spraying, plating, etc. the metal layers onto the ceramic cores. In this case, the ceramic material should preferably be formed with a flange type cross section as denoted by 226r', 228r' so that the inner and outer metal laminates do not contact each other. According to the presently preferred embodiment, the outer layers may be formed from a metal such as copper, gold, stainless steel, superalloy, or other conducting material. Preferably, the inner surface layer including the cutting edges 226b, 228b are formed from a metal which can be sharpened after the laminating process is completed. The ceramic cores 226r, 228r may be made of aluminum-oxide ceramic and nickel/aluminum coated to aid in bonding with the inner and outer metal laminates.

It will be appreciated that either of the blades 226, 228 from FIGS. 8 and 9 may be used with an opposed blade 28, 26 from FIGS. 5 and 6, or with a conventional blade 128 from FIG. 7 as explained above with reference to FIG. 7.

Figure 10:
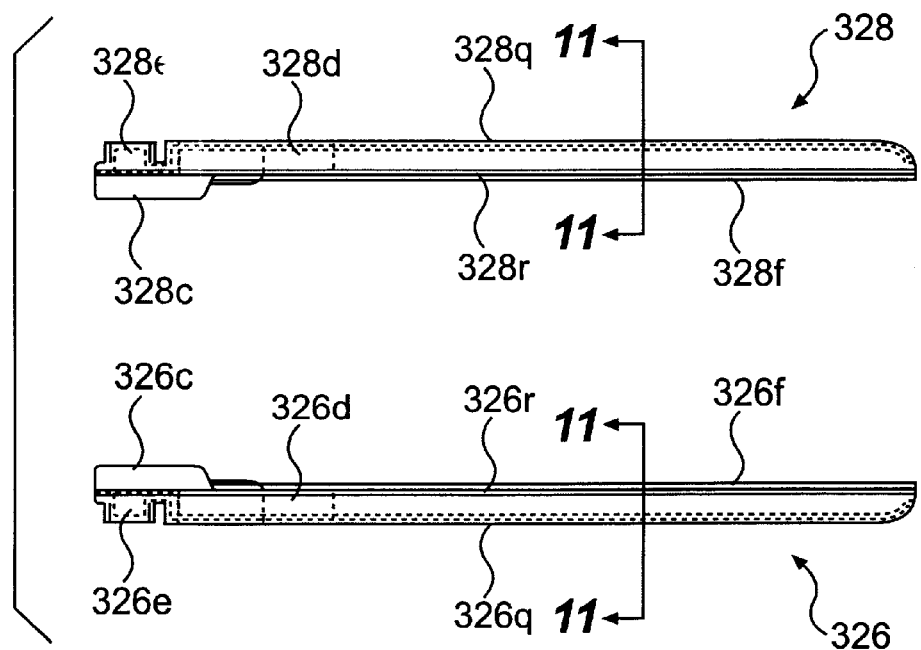
FIG. 10 is a view similar to FIGS. 5 and 8 of a third embodiment of the scissor blades according to the invention.
Figure 11:
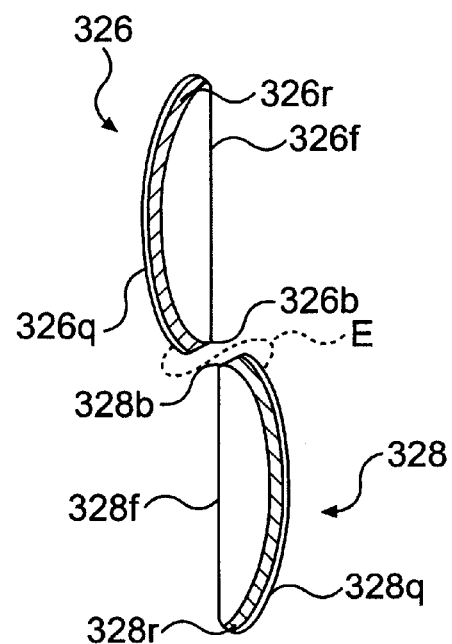
FIG. 11 is a cross sectional view of the scissor blades of FIG. 10 taken along lines 11—11 and shown in their operating positions.

FIGS. 10 and 11 show a third embodiment of scissor blades 326, 328. According to this embodiment, both scissor blades 326 and 328 are formed from metallic blades 326f, 328f which include the cutting edges 326b, 328b and shearing faces, and which are coated with a thin non-conductive layer 326r, 328r on their outer surface by gluing, glazing, spraying, depositing, firing, or otherwise fixing the non-conductive layer to the outer surfaces of the blade supports 326f, 328f. An outer metallic conductive layer or support 326q, 328q is then applied to the non-conductive layer 326r, 328r by gluing, sputtering, metalizing, thermal spraying, plating, or otherwise. The outer metallic layers 326q, 328q form the electrically conductive portions of the blades through which cautery current is applied. As seen in FIG. 10, both the insulating coating 326r, 328r and the outer metallic coating 326q, 328q extend along substantially the entire length of the blades so that electrical connection to a source of cautery current may be made at the connecting lug 326e, 328e of the blade to the outer metallic coatings 326q, 328q only. As seen in FIG. 11, the path of preferential current flow "E" is through the electrode portions 326q, 328q of the blades which are insulated from the cutting edges and the shearing surfaces of the blades. One advantage of this third embodiment is that the cutting edges 326b, 328b of the scissor blades 326, 328 are part of standard type blades 326f, 328f which are coated. Thus, the feel of the endoscopic bipolar cautery instrument should be substantially the same as the feel of non-cautery endoscopic scissors.

Again, it should be noted that either of the blades 326, 328 of the third embodiment may be utilized with an opposed blade 28, 26, 228, or 226 from FIGS. 5, 6, 8, and 9, or with a conventional blade 128 from FIG. 7 as explained above with reference to FIG. 7. It will also be appreciated that although the blades shown herein are relatively flat, curved scissor blades such as those shown in the copending application Ser. No. 08/284,793 may be used instead.

Figure 12:
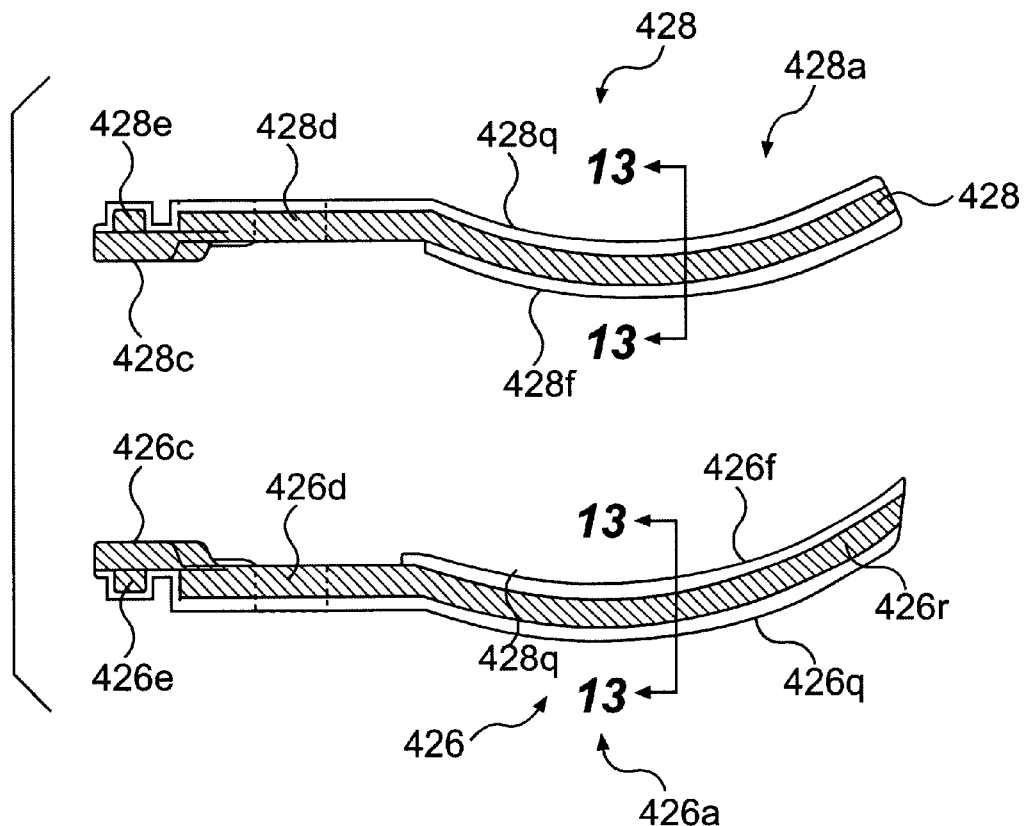
FIG. 12 is a view similar to FIGS. 5, 8, and 10 of a fourth embodiment of the scissor blades according to the invention.
Figure 13:
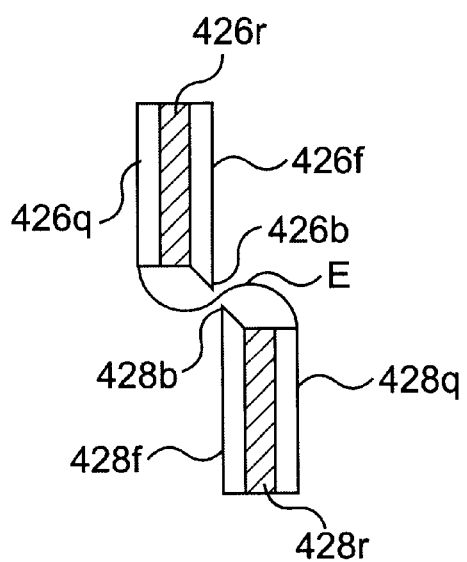
FIG. 13 is a cross sectional view of the scissor blades of FIG. 12 taken along lines 13—13 and shown in their operating positions.

A fourth embodiment of scissor blades 426, 428 is shown in FIGS. 12 and 13. The first scissor blade 426 has a curved distal portion 426a, a lower proximal tang 426c, and a mounting hole 426d therebetween. A connecting lug 426e extends orthogonally outward from the surface of the tang 426c in a first direction. As shown in FIGS. 12 and 13, the distal portion 426a includes a lower cutting edge 426b and an inner or shearing surface 426f. Behind the inner surface 426f of the first scissor blade is an insulating layer 426r, and a conducting electrode layer 426q. The opposed second scissor blade 428 is configured similarly to the first scissor blade and has a curved distal portion 428a, an upper proximal tang 428c, and a mounting hole 428d therebetween. A connecting lug 428e extends orthogonally from the surface of the tang 428c in a second direction which is opposite to the first direction mentioned above. The distal portion 428a includes a upper cutting edge 428b and an inner surface 428f. Behind the inner surface 428f of the second scissor blade 428 is an insulating layer 428r, and a conducting electrode layer 428q.

According to this fourth embodiment, both blades 426 and 428 are laminated assemblies having a non-conductive core 426r, 428r. The core 426r, 428r is preferably formed from a fiberglass or a similar material and includes the curved distal portion 426a, 428a, the proximal tang 426c, 428c, and the mounting hole 426d, 428d. A metal blade layer 426f, 428f defining a shearing surface is laminated to the inner surface of the non-conductive core 426r, 428r along the curved distal portion 426a, 428a. It will be appreciated that the metal blade layers 426f, 428f are preferably provided with sharpened opposing cutting edges 426b, 428b. An outer metallic support layer 426q, 428q is laminated to the outer surface of the non-conductive core 426r, 428r from the mounting hole 426d, 428d along the curved distal portion 426a, 428a. The outer metallic support layers 426q, 428q form the electrically conductive portions of the blades through which cautery current is applied. Thus, the outer metallic support layer 426q, 428q extends along substantially the entire length of the core 426r, 428r to make and electrical connection at the lug 426e, 428e as described above with reference to FIGS. 3–4c. As seen in FIG. 14, the path of preferential current flow "E" is through portions 426q, 428q of the blades which are insulated from the cutting edges and the shearing surfaces of the blades. It should be noted that the laminated blades of the fourth embodiment can be made more flexible than the blades of the other embodiments. It should also be noted that the laminated blades of the fourth embodiment could be provided as straight blades. Further, it will be appreciated that a straight or curved blade of the fourth embodiment can be used with any of the blades of the first, second, or third embodiments, or with a conventional blade such as shown in FIG. 7.

There have been described and illustrated herein several embodiments of bipolar endoscopic surgical scissor blades and an instrument incorporating them. While particular embodiments of the invention have been described, it is not intended that the invention be limited thereto, as it is intended that the invention be as broad in scope as the art will allow and that the specification be read likewise. Thus, while particular conductive and non-conductive materials have been disclosed, it will be appreciated that other materials could be utilized. Also, while blades of specific shape and dimension have been shown, it will be recognized that blades having different shapes and dimensions could be used with similar results obtained. While means for pivotally joining the blades has been shown as an axle screw with a nut, other pivotal joining means could be used. For example, a clevis with an integral axle pin, or a snap-in axle pin, or a riveted axle pin could all be used. While means for supplying each blade with a voltage has been shown as a bipolar push rod, it will be appreciated that other means such as a bipolar clevis and bipolar hollow tube could be used. Individual shielded electrical conductors within the hollow tube could also be used for this purpose. In addition, while the electrical coupling of the conductive portion of each blade has been shown as the proximal connecting lug which connects to a link, it will be appreciated that an electrical coupling could be made through a two piece bipolar clevis axle. Also, while the means for imparting scissor-like movement to the blades has been shown as a push rod, a pull wire or other reciprocating arrangement might be used as well. In addition, while the means for coupling the scissor blades to the push rod has been shown as an orthogonal lug, it will be understood that other means such as a connecting hole could be used while achieving substantially the same results. Moreover, while particular methods have been disclosed in reference to laminating conductive and non-conductive layers, it will be appreciated that other methods could be used as well.

What is claimed is:

1. A bipolar electrosurgical instrument for cutting and coagulating tissue comprising:
   (a) first and second metal blades each having a cutting edge and a shearing surface and supporting an insulative layer on a surface other than the cutting edge and shearing surface thereof and an electrically conductive electrode member on the insulative layer;
   (b) means for pivotally joining said first and second blades together with their respective shearing surfaces facing one another;
   (c) means coupled to at least one of said first and second blades for imparting a scissors-like movement relative to the other of said first and second blades; and
   (d) means for applying a voltage between the electrode members of said first and second blades.

2. The bipolar electrosurgical instrument as in claim 1 wherein said shearing surfaces of said first and second blades are curved.

3. The bipolar electrosurgical instrument as in claim 1 wherein said insulative layer is a ceramic material.

4. The bipolar electrosurgical instrument as in claim 1 wherein said electrode members comprise a conductive coating including metal.

5. The bipolar electrosurgical instrument for cutting and coagulating tissue comprising, in combination:
   (a) an elongated tubular member having a proximal end, a distal end, and a lumen extending therebetween;
   (b) first and second blade members, each comprising a metal blade defining a shearing surface and a non-shearing surface, a conductive layer supported by said non-shearing surface, and an intermediate, electrically insulating layer supported by the blade and disposed between said conductive layer and said non-shearing surface;
   (c) means for pivotally joining said first and second blade members to the distal end of said elongated tubular member with said shearing surfaces facing one another;
   (d) a handle affixed to said proximal end of said tubular member;
   (e) means coupled to said handle and extending through said lumen for imparting a scissors-like movement to at least one of said first and second blade members relative to one another, and
   (f) means extending through said lumen for applying a voltage between said conductive layers of said first and second blade members.

6. The bipolar electrosurgical instrument as in claim 5 wherein said intermediate electrically insulating layer is a ceramic material.

7. The bipolar electrosurgical instrument as in claim 5 wherein said first and second blade members are curved.

8. The bipolar electrosurgical instrument as in claim 5 wherein said layers comprise conductive coatings including metal.

9. The bipolar electrosurgical instrument as in claim 1 wherein each of said electrode members is a layer.

10. A bipolar electrosurgical instrument for cutting and coagulating tissue comprising:
(a) first and second metal blades each having a cutting edge and a shearing surface, said first metal blade supporting an insulative layer on a surface other than the cutting edge and shearing surface thereof and an electrically conductive electrode member on the insulative layer;
(b) means for pivotally joining said first and second blades together with their respective shearing surfaces facing one another;
(c) means coupled to at least one of said first and second blades for imparting a scissors-like movement relative to the other of said first and second blades; and
(d) means for applying a voltage between said second metal blade and the electrode member of said first metal blade.

11. A bipolar electrosurgical instrument for cutting and coagulating tissue comprising:
(a) first and second blade members, each blade member including a metal blade having a cutting edge and a shearing surface and supporting an insulative layer on a surface other than the cutting edge and shearing surface thereof and an electrically conductive electrode member on the insulative layer;
(b) means for pivotally joining said first and second blade members together with the shearing surfaces of said metal blades facing one another;
(c) means coupled to at least one of said first and second blade members for imparting a scissors-like movement relative to the other of said first and second blade members; and
(d) means for applying a voltage to the first and second blade members for providing coagulation.

12. A bipolar electrosurgical instrument for cutting and coagulating tissue comprising:
(a) first and second blade members, each blade member including a metal blade having a cutting edge and a shearing surface, said first blade member supporting an insulative layer on a surface other than the cutting edge and shearing surface thereof and an electrically conductive electrode member on the insulative layer;
(b) means for pivotally joining said first and second blade members together with the shearing surfaces of said metal blades facing one another;
(c) means coupled to at least one of said first and second blade members for imparting a scissors-like movement relative to the other of said first and second blade members; and
(d) means for applying a voltage to the first and second blade members for providing coagulation.

13. A bipolar electrosurgical instrument for cutting and coagulating tissue comprising:
(a) first and second blade members, each blade member including a metal blade having a cutting edge and a shearing surface, said first blade member supporting an insulative layer on a surface other than the cutting edge and shearing surface thereof and an electrically conductive electrode member on the insulative layer;
(b) means for pivotally joining said first and second blade members together with the shearing surfaces of said metal blades facing one another;
(c) means coupled to at least one of said first and second blade members for imparting a scissors-like movement relative to the other of said first and second blade members; and
(d) means for applying a voltage to said first blade member for providing coagulation.

14. A bipolar electrosurgical instrument for cutting and coagulating tissue comprising:
(a) first and second metal blades each having a cutting edge and a shearing surface and supporting an insulative layer on a surface other than the cutting edge and shearing surface thereof and an electrically conductive electrode member on the insulative layer;
(b) a fastener attached to and pivotally joining said first and second blades together with their respective shearing surfaces facing one another;
(c) a linkage assembly coupled to at least one of said first and second blades for imparting a scissors-like movement relative to the other of said first and second blades; and
(d) an electrical coupling connected to said electrode members for applying a voltage between the electrode members of said first and second blades.

15. A bipolar electrosurgical instrument for cutting and coagulating tissue comprising:
(a) first and second metal blades each having a cutting edge and a shearing surface, said first metal blade supporting an insulative layer on a surface other than cutting edge and shearing surface thereof and an electrically conductive electrode member on the insulative layer;
(b) a fastener attached to and pivotally joining said first and second blades together with their respective shearing surfaces facing one another;
(c) a linkage assembly coupled to at least one of said first and second blades for imparting a scissors-like movement relative to the other of said first and second blades; and
(d) an electrical coupling connected to said electrode members for applying a voltage between the electrode member and said second blade.

16. A bipolar electrosurgical instrument for cutting and coagulating tissue comprising:
first and second metal blades each having a cutting edge and a shearing surface and supporting an insulative layer on a surface other than the cutting edge and shearing surface thereof and an electrically conductive electrode member on the insulative layer;
a fastener pivotally joining said first and second blades together with their respective shearing surfaces facing one another; and
an assembly coupled to at least one of said first and second blades for imparting a scissors-like movement relative to the other of said first and second blades, wherein the assembly is configured to apply a voltage between the electrode members of said first and second blades.

17. The bipolar electrosurgical instrument as in claim 16 wherein said shearing surfaces of said first and second blades are curved.

18. The bipolar electrosurgical instrument as in claim 16 wherein said insulative layer is a ceramic material.

19. The bipolar electrosurgical instrument as in claim 16 wherein said electrode members comprise a conductive coating including metal.

20. The bipolar electrosurgical instrument as in claim 16 wherein each of said electrode members is a layer.

21. The bipolar electrosurgical instrument as in claim 16, wherein the assembly includes a rod.

22. A bipolar electrosurgical instrument for cutting and coagulating tissue comprising:
an elongated tubular member having a proximal end, a distal end, and a lumen extending therebetween;
first and second blade members, each comprising a metal blade defining a shearing surface and a non-shearing surface, a conductive layer supported by said non-shearing surface, and an intermediate, electrically insulating layer supported by the blade and disposed between said conductive layer and said non-shearing surface;
a fastener pivotally joining said first and second blade members to the distal end of said elongated tubular member with said shearing surfaces facing one another;
a handle located proximate said proximal end of said tubular member; and
an assembly coupled to said handle and extending through said lumen for imparting a scissors-like movement to at least one of said first and second blade members relative to one another and for applying a voltage between said conductive layers of said first and second blade members.

23. A bipolar electrosurgical instrument as in claim 22 wherein said intermediate electrically insulating layer is a ceramic material.

24. A bipolar electrosurgical instrument as in claim 22 wherein said first and second blade members are curved.

25. A bipolar electrosurgical instrument as in claim 22 wherein said layers comprise conductive coatings including metal.

26. A bipolar electrosurgical instrument as in claim 22, wherein the assembly includes a rod.

27. A bipolar electrosurgical instrument for cutting and coagulating tissue comprising:
first and second metal blades each having a cutting edge and a shearing surface, said first metal blade supporting an insulative layer on a surface other than the cutting edge and shearing surface thereof and an electrically conductive electrode member on the insulative layer;
a fastener pivotally joining said first and second blades together with their respective shearing surfaces facing one another; and
an assembly coupled to at least one of said first and second blades for imparting a scissors-like movement relative to the other of said first and second blades and for applying a voltage between said second metal blade and the electrode member of said first metal blade.

28. A bipolar electrosurgical instrument for cutting and coagulating tissue comprising:
first and second blade members, each blade member including a metal blade having a cutting edge and a shearing surface and supporting an insulative layer on a surface other than the cutting edge and shearing surface thereof and an electrically conductive electrode member on the insulative layer;
a fastener pivotally joining said first and second blade members together with the shearing surfaces of said metal blades facing one another; and
an assembly coupled to at least one of said first and second blade members for imparting a scissors-like movement relative to the other of said first and second blade members and for applying a voltage to the first and second blade members for providing coagulation.

29. A bipolar electrosurgical instrument for cutting and coagulating tissue comprising:
first and second blade members, each blade member including a metal blade having a cutting edge and a shearing surface, said first blade member supporting an insulative layer on a surface other than the cutting edge and shearing surface thereof and an electrically conductive electrode member on the insulative layer;
a fastener pivotally joining said first and second blade members together with the shearing surfaces of said metal blades facing one another; and
an assembly coupled to at least one of said first and second blade members for imparting a scissors-like movement relative to the other of said first and second blade members and for applying a voltage to the first and second blade members for providing coagulation.

30. A bipolar electrosurgical instrument for cutting and coagulating tissue comprising:
first and second blade members, each blade member including a metal blade having a cutting edge and a shearing surface, said first blade member supporting an insulative layer on a surface other than the cutting edge and shearing surface thereof and an electrically conductive electrode member on the insulative layer;
a fastener pivotally joining said first and second blade members together with the shearing surfaces of said metal blades facing one another; and
an assembly coupled to at least one of said first and second blade members for imparting a scissors-like movement relative to the other of said first and second blade members and for applying a voltage to said first blade member for providing coagulation.

31. A bipolar electrosurgical instrument for cutting and coagulating tissue comprising:
first and second metal blade members each having a cutting edge and shearing surface, said first metal blade supporting an insulative layer on a surface other than the cutting edge and shearing surface thereof and an electrically conductive electrode member on the insulative layer;
means for pivotally joining said first and second blades together with their respective shearing surfaces facing one another;
means coupled to at least one of said first and second blades for imparting a scissors-like movement relative to the other of said first and second blades; and
means for applying a voltage between said second metal blade and the electrode member of said first metal blade.

32. The bipolar electrosurgical instrument as in claim 31, wherein the means for pivotally joining includes a screw.

33. The bipolar electrosurgical instrument as in claim 31, wherein the means for pivotally joining includes a pin.

34. The bipolar electrosurgical instrument as in claim 31, wherein the means for applying a voltage includes a push rod.

35. The bipolar electrosurgical instrument as in claim 31, wherein the means for imparting a scissors-like movement includes a push rod.

36. The bipolar electrosurgical instrument as in claim 31, wherein the means for imparting a scissors-like movement includes a reciprocating structure.

37. The bipolar electrosurgical instrument for cutting and coagulating tissue comprising:
an elongated member having a proximal end, a distal end, and a lumen extending therebetween;

a blade assembly including first and second metal blades each having a cutting edge and shearing surface, said first metal blade supporting an insulative layer on a surface other than the cutting edge and shearing surface thereof and an electrically conductive electrode member on the insulative layer, the first and second metal blades being located proximate the distal end of the elongate member and being pivotally joined with the shearing surfaces facing one another;

a handle located at the proximal end of said tubular member; and a mechanism coupled to said handle and extending along the elongated member for imparting a scissors-like movement to at least one of said first and second blades relative to one another and for applying a voltage to the blade assembly.

38. The bipolar electrosurgical instrument as in claim 37, wherein the mechanism applies the voltage between the electrically conductive electrode member and the second metal blade.

39. The bipolar electrosurgical instrument as in claim 37, wherein the mechanism includes a rod assembly extending through the lumen.

40. The bipolar electrosurgical instrument as in claim 37, further comprising a fastener pivotally joining the first and second metal blades.

* * * * *

UNITED STATES PATENT AND TRADEMARK OFFICE
CERTIFICATE OF CORRECTION

PATENT NO.    : 6,447,511 B1
DATED         : September 10, 2002
INVENTOR(S)   : Charles R. Slater Page 1 of 1

It is certified that error appears in the above-identified patent and that said Letters Patent is hereby corrected as shown below:

Column 12,
Line 27, after "than" insert -- the --.
Line 40, "members" should read -- member --.
Line 41, after "second" insert -- metal --.

Column 13,
Line 26, "A" should read -- The --.
Line 29, "A" should read -- The --.
Line 31, "A" should read -- The --.
Line 34, "A" should read -- The --.

Column 14,
Line 36, "blade members" should read -- blades --.
Line 64, "The" should read -- A --.

Signed and Sealed this

Fourth Day of February, 2003

JAMES E. ROGAN
*Director of the United States Patent and Trademark Office*